United States Patent
Mahant et al.

(10) Patent No.: US 6,821,790 B2
(45) Date of Patent: Nov. 23, 2004

(54) METHODS AND APPARATUS FOR SEPARATION OF BIOLOGICAL FLUIDS

(76) Inventors: Vijay Mahant, 42299 Wild Mustang Rd., Murrieta, CA (US) 92562; Byron Doneen, 2042 Corte del Nogal, Carlsbad, CA (US) 92009

( * ) Notice: Subject to any disclaimer, the term of this patent is extended or adjusted under 35 U.S.C. 154(b) by 325 days.

(21) Appl. No.: 09/949,314

(22) Filed: Sep. 7, 2001

(65) Prior Publication Data

US 2002/0052008 A1 May 2, 2002

Related U.S. Application Data

(63) Continuation-in-part of application No. 09/514,686, filed on Feb. 28, 2000, now Pat. No. 6,291,249, and a continuation of application No. 09/261,068, filed on Mar. 2, 1999, now abandoned.

(51) Int. Cl.[7] .................................................. B03C 1/00
(52) U.S. Cl. ........................ 436/177; 436/178; 436/520; 436/526; 436/535; 435/7.2; 435/7.23; 435/7.24; 435/4.25; 435/287.9; 435/288.1; 435/288.2; 435/288.3; 435/288.4; 435/288.5; 435/288.6; 422/56; 422/57; 422/58; 422/59; 422/60; 422/61; 422/44; 422/48; 422/77; 422/101; 422/102; 210/222; 210/223; 210/451
(58) Field of Search ................................. 435/7.2, 7.23, 435/7.24, 7.25, 287.9, 288.1, 288.2, 288.3, 288.4, 288.5, 288.6; 436/177, 178, 520, 526, 535; 422/56, 57, 58, 59, 60, 61, 44, 48, 77, 101, 102; 210/222, 223, 457

(56) References Cited

U.S. PATENT DOCUMENTS 6,291,249 B1 * 9/2001 Mahant et al. .............. 436/177

OTHER PUBLICATIONS

Durcova et al., Immunomagnetic isolation of mouse embryonic stem cells from heterogeneous cell population, Journal of Reproduction and Development, 44 (1): 85–89 (Feb. 1998) (Abstract).*

Przyborski, Isolation of human carcinoma stem cells by immunomagnetic sorting, Stem Cells 19 (6) 500–504 (2001) (Abstract).*

* cited by examiner

Primary Examiner—Christopher L. Chin
Assistant Examiner—Gailene R. Gabel
(74) Attorney, Agent, or Firm—Rutan & Tucker

(57) ABSTRACT

A method of separating a cell-containing sample into a substantially cell-depleted portion, and a cell-containing portion comprising at least one of a stem cell, a lymphocyte, and a leukocyte comprises a step in which the sample is received in a vessel with at least one flexible wall. In another step, an additive and particles are added to the sample, wherein the additive substantially binds to the at least one of the stem cell, lymphocyte, and leukocyte, and the particles and wherein the particles substantially bind to the at least one of the stem cell, lymphocyte, and leukocyte, and the additive, thereby producing a cell-containing network. In a further step, the network is separated from the substantially cell-depleted portion by applying a magnetic force.

12 Claims, 2 Drawing Sheets

METHODS AND APPARATUS FOR SEPARATION OF BIOLOGICAL FLUIDS

This application is a continuation-in-part of allowed U.S. patent application Ser. No. 09/514,686, filed Feb. 28, 2000, now U.S. Pat. No. 6,291,249 and is a continuation-in-part of U.S. patent application Ser. No. 09/261,068 filed Mar. 2, 1999, now abandoned, both of which are incorporated herein by reference herein.

FIELD OF THE INVENTION

The field of the invention is clinical diagnostics and biotechnology.

BACKGROUND OF THE INVENTION

In vitro diagnostic tests to identify and treat diseases have become common tools in hospitals, homes and physician's offices. Biological fluids such as blood, urine or cerebrospinal fluids, which may at times contain blood, are the most frequently employed biological samples for such tests.

Blood contains many different components, some of which are present in strikingly varied concentrations from sample to sample. The percentages of both red and white blood cells in whole blood, for example, can vary among normal individuals, and even in the same individual over time, and in particular under pathological conditions. This large variation coupled with other factors such as storage conditions, coagulation, and the fragility of red blood cells, produces considerable technical problems in performing diagnostics using blood-containing samples.

Whole blood is usually separated into various fractions prior to testing. Among other things, separation into fractions can advantageously compensate for differences in hematocrit values, and in other ways reduce potential interference in up stream or down stream biochemical assays. Frequently employed fractions are serum, plasma, white cells, red blood cells and platelets. The terms "plasma" and "serum" are used herein to mean any fluid derived from whole blood from which a substantial portion of the cellular components has been removed. Plasma and serum are used herein interchangeably, because the presence or absence of coagulants is not a critical factor.

Blood separation technologies can be conceptually grouped into three categories—centrifugation, filtration, and solid-phase separation.

Centrifugation

Blood separation is routinely achieved by centrifugation. Centrifugation is generally desirable because: (1) centrifugation can generally separate cellular components from serum or plasma at an efficiency of greater than 95%; (2) centrifuges do not require highly trained personnel to operate; and (3) centrifugation allows concurrent processing of multiple samples in under 15 minutes. Centrifugation of blood is, however, also problematic. For example, centrifuges are expensive, involve multiple steps, are often unavailable at points of care such as bedside, schools or at home, and usually require electrical power for operation.

Filtration

Many filtration techniques are known for separating various components from blood. U.S. Pat. No. 4,987,085 to Allen et al., for example, describes a filtering system with descending pore size using a combination of glass fiber membranes and cellulose membranes. U.S. Pat. No. 4,753,776 to Hillman et al. discloses a glass microfiber filter using capillary force to retard the flow of cells. U.S. Pat. No. 4,256,693 to Kondo et al. discloses a multilayered chemical analysis element with filter layers made from at least one component selected from paper, nonwoven fabric, sheet-like filter material composed of powders or fibers such as man-made fibers or glass fibers. U.S. Pat. Nos. 3,663,374 and 4,246,693 disclose membrane filters for separating plasma from whole blood and U.S. Pat. Nos. 3,092,465, 3,630,957, 3,663,374, 4,246,693, 4,246,107, 2;330,410 disclose further filtration systems, some of which make use of small-pore membranes.

Known filtration techniques generally reduce the volume of blood required to only a few drops. Many filtration tests therefore contemplate using only about 25 to 75 $\mu$l of whole blood. Some filtration techniques have even been developed that require only about 5 to 50 $\mu$l of whole blood. In most applications, filtration occurs directly on a test-strip in which the filtration surface is placed above the reaction zone or zones of the strip. Filtration in these formats also reduces or eliminates the availability problems associated with centrifuges.

But these advances often create entirely new problems. For example, filters tend to retain significant amounts of plasma, and analytes present in low concentrations are frequently difficult to detect in the serum derived from small volumes of blood. Existing filters also tend to clog, and have undesirably slow flow rates. Agglutinating agents are often mixed with whole blood to reduce clogging and to improve flow rates, (see U.S. Pat. Nos. 5,262,067, 5,766,552, 5,660, 798 and 5,652,148), but these problems remain.

Efforts have been made to improve the flow rate by modifying the force employed against the filter. But choices here are fairly limited. Filters are relatively simple to produce and use, but tend to cause excessive hemolysis of red blood cells. Capillary action, a phenomenon in which water or liquid will rise above normal liquid level as a result of attraction of molecules in liquid for each other and for the walls of a capillary can also be used. Capillary action, however, is generally too weak to effect rapid separation of large volumes. (See, for example, U.S. Pat. Nos. 5,660,798, 5,652,148 and 5,262,067). Moreover, separation of plasma by capillary action tends to retain a relatively large amount of fluid within the wicking membrane, or a collection membrane. This in turn may necessitate testing the wicking membrane or the collection membrane or both, or eluting the retained material from the membranes.

Solid-Phase Separation

Solid-phase separation typically involves a surface having binding to a target, the surface acting to immobilize and remove the target from a sample. Exemplary solid-phase separation techniques are binding chromatography, binding separation using beads, and hollow fibers separations.

One particularly advantageous type of solid-phase separation is magnetic separation, in which a target is captured by magnetically attractable (paramagnetic) beads. Since no physical barriers are present, as would be the case with filtration separation, magnetic separation tends to be relatively gentle. In U.S. Pat. No. 5,514,340 to Lansdorp and U.S. Pat. No. 5,123,901 to Carew, for example, magnetic wires are employed in batch processes to separate magnetic particles from a fluid. In U.S. Pat. No. 4,663,029 to Kelland et al. and U.S. Pat. No. 5,795,470 to Wang, magnetic particles are separated out from a fluid in a continuous flow process. Still other methods published for example in U.S. Pat. No. 5,536,475 to Moubayed, employ rocking separation chambers and multiple magnets to separate magnetic particles from a fluid.

One of the major limitations of applying known magnetic separation to blood separation is that multiple anti-ligands are required to remove all of the various types of cells and sub-cellular particles. Red blood cells, lymphocytes, monocytes, and platelets, for example, have different surface antigens, and do not specifically bind to any one antibody. Furthermore, lack or absence of ligands on the cells due to pathological conditions, genetic diseases or genetic variations or life cycle of cells generally reduce the efficiency with which the anti-ligands bind with the target cells.

The problems with known magnetic separation devices are exacerbated with increasing sample volumes, especially sample volumes over one milliliter. Since many diagnostic applications require serum volumes of up to one milliliter to satisfy the requirements of multiple tests or batteries of tests, magnetic separation has not been particularly useful. Moreover, assays such as glucose or hemoglobin tests are highly susceptible to interference caused by biological or chemical substances in the sample, including proteins, bilirubin, and drugs.

Thus, there is still a need to provide improved methods and apparatus for separating blood into its constituent parts, and especially for separating plasma or serum from whole blood.

SUMMARY OF THE INVENTION

In accordance with the present invention, a cell-containing sample is separated into a cell-containing portion and a substantially cell-depleted portion, by mixing the sample with both an additive and particles to produce a cell-containing network, and separating the network from the remaining substantially cell-depleted portion using a magnetic force.

In one aspect of preferred embodiments the vessel has a plurality of confining walls, and at least one of the confining walls is flexible. The sample is retained within the confining walls, preferably comprises whole blood, and the cell-containing portion largely comprises a network of inter-linked red blood cells, stem cells, leukocytes, or lymphocytes. Especially preferred linkers include anti-ligands such as primary antibodies that bind to a ligand or an antigen on or in the cell membranes of the cells to be isolated/separated, and secondary antibodies that bind to the primary antibodies. In another aspect of preferred embodiments, the primary antibodies are added directly to the sample, and the secondary antibodies are coupled to the surfaces of paramagnetic beads.

In another aspect of preferred embodiments, polymeric materials such as Polybrene®, cationic liposomes, cationic lipids, and polydendromers may be used in combination with anti-ligand(s) and magnetic separation or in combination with anti-ligand(s) and filtration. Aptamers can be used as anti-ligand(s) by themselves or in combination with cationic polymers, cationic liposomes, and dendromers.

In yet another aspect of preferred embodiments, the separation takes place within the confining walls, and while in some embodiments the separation employs at least in part a magnetic force, in other embodiments at least two forces are employed to separate the network from the substantially cell-depleted portion. Where two forces are employed for separation, one force is a magnetic force and another force is an electromechanical force transmitted through at least one confining wall, wherein the terms "electromechanical", "automatic", "hydraulic" and "pneumatic" are used interchangeably herein.

Various objects, features, aspects and advantages of the present invention will become more apparent from the following detailed description of preferred embodiments of the invention, along with the accompanying drawings in which like numerals represent like components.

DETAILED DESCRIPTION OF SPECIFIC EMBODIMENTS

Figure 1A:
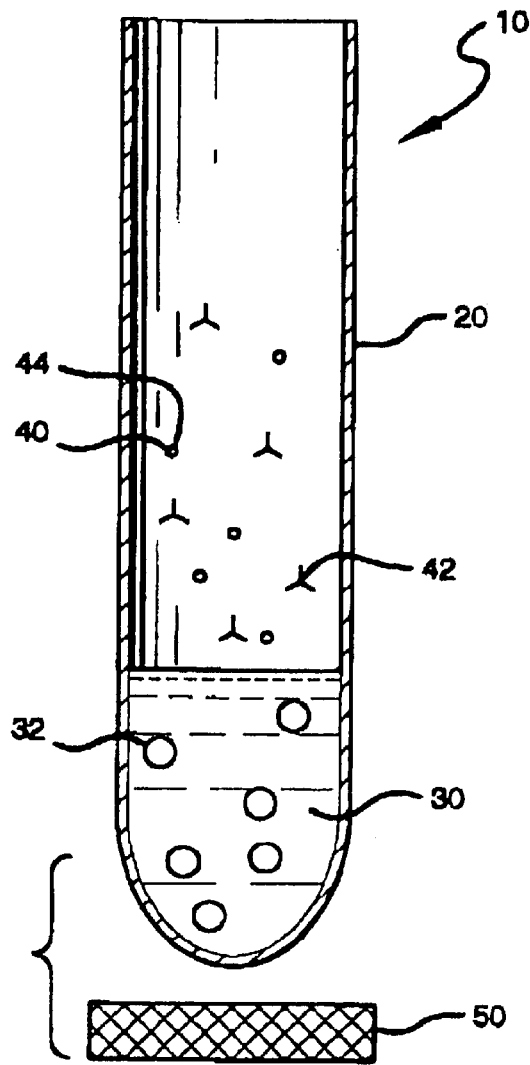
FIG. 1A is a schematic of a preferred embodiment in which separating agents are being added to a blood sample.

In the generalized preferred embodiment of FIG. 1A, a blood separation apparatus 10 comprises a vessel 20 and a magnet 50. The vessel 20 contains blood 30, to which is being added primary antibodies 42 having a substantial binding to cells, and particles 40 coated with a secondary antibody having a substantial binding to primary antibodies 42.

Vessel 20 is preferably an ordinary test tube or test tube-like vessel such as a vacutainer or falcon tube. The volume of such tubes is preferably less than about 10 ml, although it is contemplated that appropriate vessels may define sample cavities of greater or lesser volumes.

Although vessel 20 is depicted as having a typical test-tube shape, alternative vessels are contemplated to have different shapes. Thus, suitable vessels may have a narrowed top portion to facilitate recovery of the substantially red blood cell-depleted portion. Alternative vessels may also have differently shaped bottoms, such as a V-shaped or a flat bottom. In yet another example, an individual vessel may be formed as part of an array, such as in a multi-well microtiter plate. Further examples of suitable vessels include, hollow fibers, arrays of capillaries, beakers, pouches, dishes and cylinders—generally any device that can retain fluid within confining walls, and provide at least one opening. Appropriate vessels are even contemplated to include "open walled" structures such as a microscope slide having micro-channels etched on glass or plastic, or a simple plastic foil or film.

It is specifically contemplated that vessels employed in conjunction with the teachings herein retain a sample within a plurality of confining walls, and that at least one of the confining walls is flexible. The term "flexible" confining wall as used herein refers to a wall that can be substantially deformed employing moderate pressure (i.e., less than 0.5 psi) without breaking or otherwise damaging the confining wall. For example, a plastic foil or thin latex sheet are considered flexible. In contrast, a typical thin (2 mm) polycarbonate plate would not be considered flexible under the scope of this definition, because polycarbonate plates can typically not be substantially deformed without breaking. Particularly contemplated vessels may therefore have one relatively rigid wall onto which at least one other confining flexible wall with individual compartments is mounted (e.g., a thin plastic sheet by heat sealing), and in even more particularly contemplated vessels, all of the confining walls may be flexible. Such vessels may have envelope shape and examples of contemplated vessels are described in U.S. patent application Ser. No. 09/272,234, which is incorporated herein by reference.

It is contemplated that vessels can be made from any appropriate material or materials, including glass, synthetic polymers, ceramics, metals, or mixtures thereof. Such vessel can be colored or transparent, translucent or non-translucent, and may or may not have graduation or other markings.

In FIG. 1A the sample being separated is whole blood. Such blood is generally contemplated to be fresh human whole blood, a few milliliters of which are preferably obtained by venipuncture. Another example is capillary blood, which can be obtained in volumes ranging from less than 10 to hundreds of $\mu$Ls by use of a lancet. Furthermore, it is contemplated that sample volumes higher than a few microliters to a few milliliters can be used, especially where a relatively high number of cells is desired. For example, where lymphocytes are separated for use in a post-radiation transfusion in a cancer patient, suitable sample volumes may be substantially higher than a few milliliters. Similarly, where stem cells for organ regeneration are separated, the sample volume will likely exceed 50 ml and more. Therefore, contemplated volumes will typically be in the range of about 1–10 mL, more typically in the range of 10–100 mL, and most typically in the range of about 100–500 mL (and even more).

The blood can be pre-treated, such as by addition of an additive, or removal of a component. Contemplated additives include buffer, water or isotonic solution, anticoagulants, antibodies, and test solutions. Contemplated substances or components that can be removed include antibodies, globulins, albumin, and cellular fractions such as platelets, white blood cells etc.

The blood can also be derived from non-human sources, including vertebrate or invertebrate animals. Blood employed as set forth herein can also be taken from any type of storage, and as such may be cooled blood, frozen blood, or blood with preservatives.

In preferred embodiments, the primary antibodies 42 are mouse derived monoclonal anti-bodies to human red blood cells, which in the field would often be referred to as monoclonal Ab to hRBCs. The secondary antibodies 44 are preferably sheep, donkey, goat, or mouse derived anti-mouse IgG antibodies.

Techniques for raising the antibodies are well known. For example, both the primary and secondary antibodies can be derived from any appropriate source including, goat, sheep, horse or recombinant sources. Suitable antibodies can also be selected from many classes and subclasses, including IgG and IgM, and subclasses. Furthermore, antibodies can be selected from numerous molecular varieties, including proteolytic fragments or engineered fragments such as Fab or (Fab)$_2$, or chimeric antibodies. Combinations of antibodies are specifically contemplated.

Of course, both primary and secondary antibodies would advantageously have substantial binding to their respective targets. The primary antibodies would preferably have substantial binding to red blood cells, and in particular would have substantial binding to at least one ligand or component present on a surface of the red blood cells. The secondary antibodies would preferably have substantial binding to at least some component of the primary antibodies.

The secondary antibodies 44 are preferably included in the coating of coated particles 40. Such particles are attractable by magnetic force, and preferably comprise a paramagnetic composition embedded in synthetic polymers or cellulose. Although paramagnetic particles are preferred, the coated particles can also or alternatively include ferromagnetic or chromium material or mixtures thereof. In still further variations, suitable particles can be coated with many other materials including natural or synthetic polymers, agarose etc. The preferred particle size is in the range of 0.1–100 $\mu$m, but alternative sizes between 10–100 nm or larger than 100 $\mu$m are also contemplated. Viewed from another aspect, it is contemplated to employ particles having a mean volume between about $5 \times 10^{-24}$ m$^3$ and about $5 \times 10^{-6}$ m$^3$. Where red blood cells are being targeted, the diameter of the red cells may advantageously be about five times the diameter of the coated particles.

The term "coated" is used herein to mean any complete or partial covering of any exposed surface. In FIG. 1, the particles 40 are coated with a material that immobilizes the secondary antibodies. Such immobilization can be temporary or permanent, and can involve covalent or non-covalent binding. For example, non-covalent binding may involve incubating antibodies with the bead or other solid-phase. As another example, covalent coupling of antibodies to a solid-phase may involve including reacting amino groups of an antibody with aldehydes on the solid-phase, or activated carboxyl groups on the solid-phase, resulting in a covalent bond.

In yet other embodiments, one or both of the primary and secondary antibodies can be replaced by or complimented with an alternative composition have the desired binding, and at least a minimally acceptable specificity. Anti-ligands are a general class of such alternative compositions, and are defined herein as any molecule that binds non-covalently to an appropriate ligand. Examples of anti-ligands and ligands include and are not limited to antibodies and antigens, respectively, and sense and anti-sense oligonucleotides in nucleic acids. Other polymers are contemplated as well as nucleotides. Additional examples are aptamers and lectins having a substantial binding to ligands.

The term "a cell-containing network" refers herein to an aggregate of at least more than one cell, from which individual cells cannot readily be mechanically removed without lysing the removed cells. Normally clotted blood is one example of a cell-containing network, but aggregates formed substantially by any combination mediated by molecular interactions such as hydrophobic-, hydrophilic-, electrostatic-, van-der-Waals-, ionic interaction or other molecular interactions are also contemplated. Thus, other examples of cell-containing networks are aggregates of red, white or other cells formed by combinations with antibodies or other linking agents having substantial binding to the cells. It is especially contemplated that such networks may include solid supports such as beads.

It is especially contemplated that heterogeneous aggregates can be formed using a mixture of red blood cells with two different antibodies, wherein the primary antibody binds the red blood cells, and the secondary antibody binds to the primary antibody. If only one of the two binding portions of the antibody is involved in such binding, the following aggregates can be formed: (a) primary antibody bound to a red blood cell; (b) secondary antibody bound to the a primary antibody only; and (c) secondary antibody bound to primary antibody that is bound to a red blood cell or some other cell type in blood or body fluids. If both of the two binding portions of the antibodies are involved in binding, any combination of the aggregates (a), (b), (c) may be formed, thereby producing a potentially vast network of aggregates.

The sample, antibodies or other anti-ligands, and beads or other particles may be combined in the vessel in any order. For example, in one class of embodiments (not shown), vessels are contemplated to be pre-loaded with magnetically attractable beads. Suitable such vessels are commercially available as MiniMACS™ separation columns from Miltenyi Biotec™, and the columns are even provided with a separation enhancing device. The standard protocol would need to be modified to conform to the teachings herein, such as by pre-coating the beads with an appropriate anti-ligand, and by adding an appropriate anti-ligand to the sample.

The magnet 50 is generally a disc magnet, but in alternative embodiments the magnet can also have different shapes and designs. Contemplated alternative magnets include bar magnets, horseshoe magnets, ring magnets, and can have any suitable multiple pole geometry including quadrapoles, hexapoles and octapoles, etc. Magnets can be of the permanent type, electromagnets, or even superconducting magnets, and may comprise ferromagnetic or rare earth magnets. Furthermore, the magnet need not be a single magnet, but can advantageously comprise a plurality of magnets. Preferred magnets have strengths in the range of 0 to 2 Tesla for permanent magnets, or 0–100 Tesla for electromagnets. Especially preferred magnets employ a permanent magnet of field strength 0 to 1 Tesla.

In further alternative aspects of the inventive subject matter, the sample is retained within a plurality of confining walls, and the separation takes place within the plurality of confining walls employing a first and a second force. While the first force comprises a magnetic force (vide supra), the second force comprises an automatic mechanical force that is transmitted through at least one of the confining walls. As used herein, the term "automatic" mechanical force is used herein to refer to a process in which a mechanical force is applied in a manner other than manually applying a force. In particularly contemplated embodiments, the automatic mechanical force comprises a pressure that is applied to a flexible confining wall. For example, in a vessel wherein all of the confining walls are flexible, a magnetic force may retain the network within the confining walls, while a mechanical force (e.g., one or more actuators compressing the vessel) assist in separation of the network from the substantially cell-depleted portion.

Figure 1B:
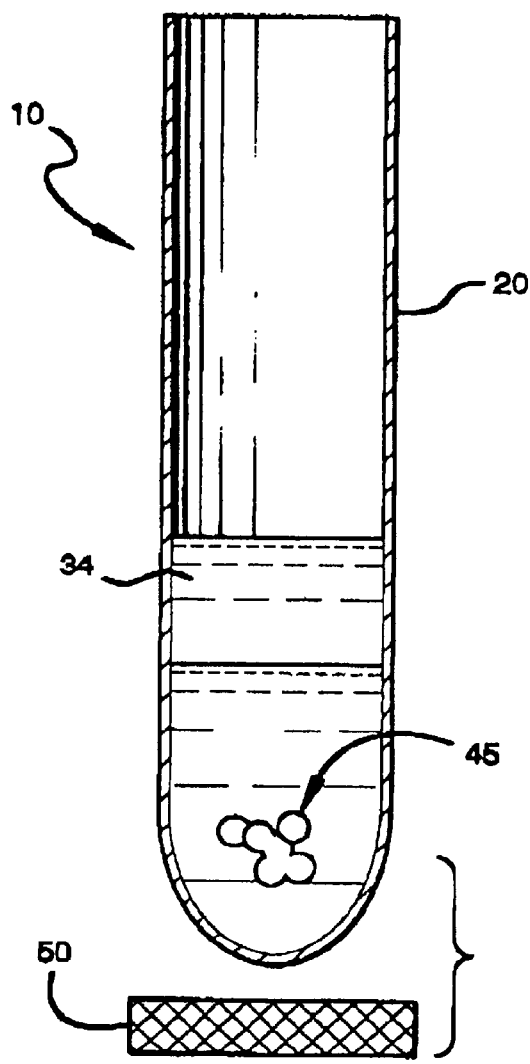
FIG. 1B is a schematic of the embodiment of FIG. 1A following separation of red blood cells.

In FIG. 1B several networks 45 have been formed from the blood cells 32 (not shown in detail), antibody coated paramagnetic particles 40 (not shown in detail), and anti-red blood cell antibodies 42 (not shown in detail). The particles 40 within the network 45 are being attracted by magnet 50, thereby separating out the cell-containing networks 45 from the substantially cell-depleted plasma 34.

Red blood cells 32 are generally mature non-nucleated erythrocytes. These blood cells usually are the predominant form of red blood cells present in a sample. In alternative embodiments, red blood cells can also be red blood cells carrying any type of hemoglobin including α, β, γ or fetal hemoglobin. The red blood cells can also be regular healthy blood cells or red blood cells giving raise to diseases e.g. sickle cell anemia or thalassemia. Appropriate red blood cells can also be in many stages of development, e.g. nucleated erythioblasts or aged, non-nucleated erythrocytes.

The inventive subject matter is, of course, not limited to mature non-nucleated erythrocytes, and specifically contemplates other stages of red cell development, other cells including white cells, and even cellular fragments including platelets. Thus, for example, where the sample comprises urine, a clinician or other individual may employ the inventive methods and apparatus to separate out bacterial cells or sloughed off bladder or urethral cells, and in such instances the red cells 32 of FIG. 1B may be replaced with non-erythrocytes.

Alternatively, various non-red blood cells may of particular interest, especially where such cells are separated for further clinical, experimental, or diagnostic use. Among particularly contemplated alternative non-red blood cells, various stem cells, lymphocytes, and leukocytes are especially preferred. The term "stem cell" as used herein refers to a cell that gives rise to a lineage of cells, and that may be characterized as a cell that upon division, produces dissimilar daughters, one replacing the original stem cell, the other differentiating further. While it is generally preferred that contemplated stem cells are undifferentiated stem cells, partially differentiated stem cells are also contemplated. Thus, suitable stem cells include embryonic stem cells, umbilical cord blood stem cells, and adult/peripheral stem cells. Consequently, the source of contemplated samples for use herein may vary considerably and may include blood, tissue samples (e.g., skin), commercially available stem cells and stem cell lines, and embryonic tissue. It is further contemplated that stem cells isolated by contemplated methods may be useful in a variety of clinical and research settings, and particularly preferred uses include at least partial regeneration of diseased or necrotic organs or organ substructures, research into differentiation signals and pathways, etc.

Where isolated non-red blood cells are leukocytes, all subtypes of white blood cells are generally contemplated suitable and include neutrophiles (polymorphs), lymphocytes, eosinophiles, and basophiles. Of particular interest are lymphocytes (i.e., white cells of the blood that are derived from stem cells of the lymphoid series), and especially various B cells, T cells, T helper cells, and memory B cells. Such cells may be obtained from numerous sources, however, it is generally contemplated that the most common source are blood, amniotic fluid, and bone marrow aspirate. Thus, it is contemplated that leukocytes or lymphocytes may be obtained from any appropriate source (typically, the sample is taken from a mammal, and more preferably, from a human).

It is further contemplated that all markers that can both (i) form a specific interaction for a desired cell type and (ii) allow a specific interaction with a high affinity binding partner can generally be used for separation of the desired cell type. As used herein, the term "high affinity binding partner" refers to an affinity of $K_d < 10^{-4}$ mol$^{-1}$. Consequently, numerous markers other than red blood cell markers (e.g., glycophorin A) are suitable for use herein, and an exemplary collection of suitable markers for various stem cells, leukocytes, and lymphocytes for use in separation is provided in Table 1, below.

| Marker | Synonyms | Specificity |
|---|---|---|
| Leukocyte Markers (general) | | |
| CD 1 | | Thymocytes, Langerhans histiocytes |
| CD 33 | | Myeloid progenitor and monocytes |
| S100 | | Interdigitating dendritic cells of the lymph node paracortex. |
| CD 45 | LCA, leukocyte common antigen | All leukocytes |
| CD 30 | Ki-I | Activation marker for B, T, and monocytes |

-continued

| Marker | Synonyms | Specificity |
|---|---|---|
| *T-Cell markers* | | |
| CD 2 | | T and NK cells |
| CD 3 | | All thymocytes, T and NK cells |
| CD 4 | | Helper T cells |
| CD 5 | | All T cells, some B cells |
| CD 7 | | All T cells, some myeloid cells |
| CD 8 | | Cytotoxic T cells |
| CD 16 | | NK cells and granulocytes |
| *B-Cell markers* | | |
| CD 10 | CALLA Common acute lymphocytic leukemia antigen | Early precursor and pre-B cells |
| CD 19 | | preB, B cells, but not plasma cells |
| CD 20 | L26 | preB, but not plasma cells |
| CD 21 | EBV-R | Mature B and follicular dendritic cells |
| CD 22 | | Mature B |
| CD 23 | | Activated marrow B |
| *Other specific and general markers* | | |
| CD 15 | Leu M2 | All granulocytes, Reed Sternberg cells |
| CD 34 | | Early pluripotent progenitor cell |
| CD 61 | platelet glycophorin | Associated with M7 AML |
| EMA | epithelial marker antigen | Epithelial cells |
| TdT | | T and B lymphocytes, lost before maturity |
| *Stem Cell Markers* | | |
| SSEA-3 | | Primate embryonic stem cells |
| SSEA-4 | | Primate embryonic stem cells |
| TRA-1-60 | | Primate embryonic stem cells |
| TRA-1-81 | | Primate embryonic stem cells |
| Sca-1/Thy-1.1 lo | | Hematopoietic stem cells Hematopoietic stem cells |

Where a particular antibody or affinity reagent for a marker for a desired stem cell, leukocyte, or lymphocyte is not commercially available, it is contemplated that suitable antibodies or antibody fragments may be raised using standard procedures well known in the art (see e.g., Monoclonal Antibody Protocols (Methods in Molecular Biology, 45) by William C. Davis; Humana Press; ISBN: 0896033082).

It should still further be appreciated that cells bound to the high affinity binding partner (e.g., antibody or antibody fragment) can be released from such binding partners using a variety of techniques well known in the art, and particularly contemplated methods of release include competition with excess of antigen or epitope to which the high affinity binding partner is specific, high temperature treatment, acidification (e.g., pH<3.5), proteolysis, and mild chaotropic agents. Where it is desirable that an isolated cell is removed from the magnetic bead without separation of the high affinity binding partner from the cell, various methods of breaking a covalent bond between a high affinity binding partner and a magnetic particle are contemplated. Among such methods, reductive cleavage of a disulfide bond, or enzymatic cleavage (e.g., via an peptidase) of a bond in a linker connecting the high affinity binding partner to the magnetic particle are particularly preferred. Exemplary methods of removing a hapten from an antibody are described in Affinity Chromatography Methods and Protocols (Methods in Molecular Biology) by Pascal Bailon, George K. Ehrlich, Wen-Jian Fung, wo Berthold, Wolfgang Berthold (Humana Press; ISBN: 0896036944), or in Handbook of Affinity Chromatography by Toni Kline (Marcel Dekker; ISBN: 0824789393).

In addition to operating on a wide variety of samples, it is also contemplated that the inventive methods and apparatus described herein can be employed to measure a wide variety of analytes. Contemplated analytes include tumor markers such as prostate specific antigen (PSA), infectious disease markers, endocrine markers such as testosterone, estrogen, progesterone and various cytokines, and metabolic markers such as creatinine, glucose.

Figure 2A:
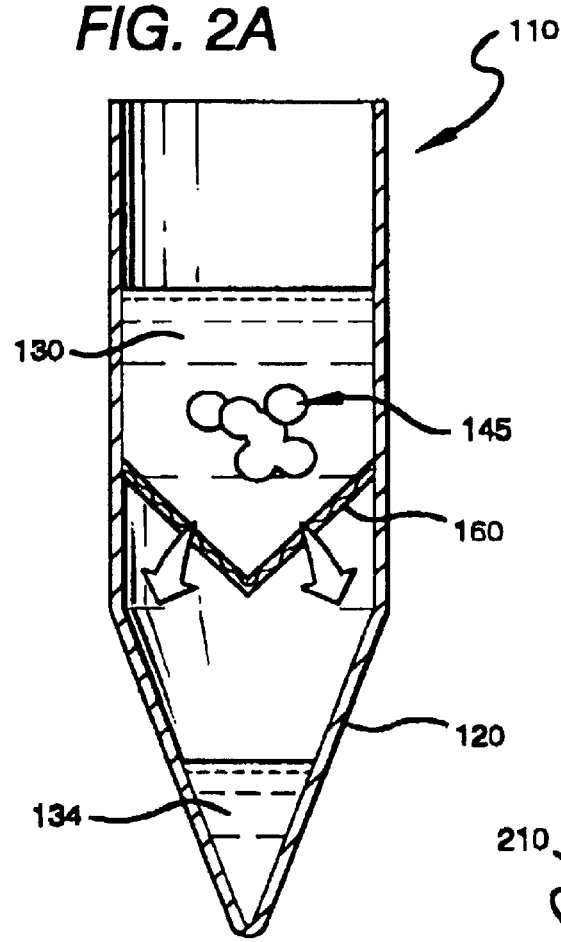
FIG. 2A is a schematic of an alternative embodiment.

In FIG. 2A a blood separation apparatus 110 has a soft-walled or otherwise flexible vessel 120 containing a network 145 formed from whole blood 130 comprising red blood cells 132 (not shown in detail), anti-red blood cell antibodies 142 (not shown in detail)and anti-mouse antibodies 144 (not shown in detail). A filter 160 filters out the network 145, and allows plasma 134 to pass through to a collection area.

The filter 160 is preferably a glass fiber filter having a pore size below the size of the cellular components of blood or larger than the individual cells, but smaller than the network. In alternative embodiments the filter can be made from many materials including chromatographic paper, natural or synthetic fibers, porous membranes etc. Examples for those alternative filters are nylon fiber filters, size exclusion membranes, paper filters, woven fabric filters. Furthermore, the filters may or may not be coated with material e.g. to reduce hemolysis or to specifically retain selected fractions or molecules. Appropriate coatings include polyvinylalcohol, polyvinylacetate, polycationic polymers, lectins or antibodies.

In FIG. 2A the filtrate portion of the sample is passed through the filter by gravity. However, it is recognized that the driving force to move the sample through the filter can be a force or pressure differential across the membrane, and can be achieved in many ways including centrifugation, vacuum, compressed gas, or a magnet as described elsewhere herein. The filtration time can vary greatly, but is generally considered to be within the range of a few seconds to less than 30 min. Of course it should be appreciated that such separation characteristics and efficiency may also be obtained from various cells, other than red blood cells, including for example, leukocytes, lymphocytes, and stem cells.

Figure 2B:
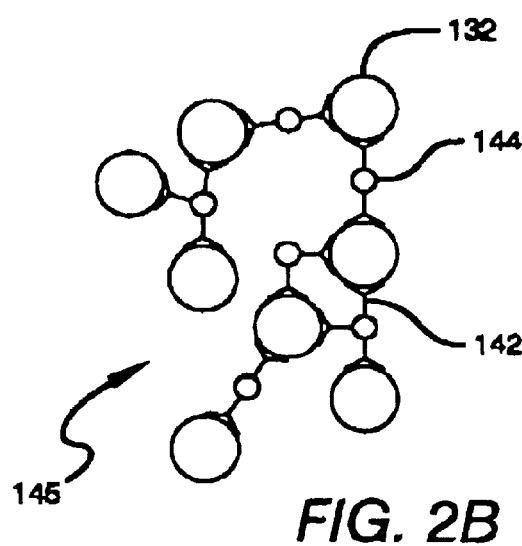
FIG. 2B is a schematic of binding interactions contemplated to be present in the embodiment of FIG. 2A.

FIG. 2B depicts details of a possible portion of network 145, which includes anti-red blood cell antibodies 142 bound to red blood cells 132, and anti-mouse antibodies 144 bound to anti-red blood cell antibodies 142. Those skilled in the art will recognize that a single network can contain millions of cells, and it should be appreciated that the orientation and connections of the various components in FIG. 2B are purely exemplary, and would not necessarily ever be found in an actual network. Among other things, a real-life network would be three-dimensional, rather than the two dimensional schematic as shown, and the antibodies would be much smaller than that shown in the drawing. It should also be appreciated that network 45 of FIG. 1B is contemplated to have corresponding structures to that depicted in FIG. 2B.

Figure 3:
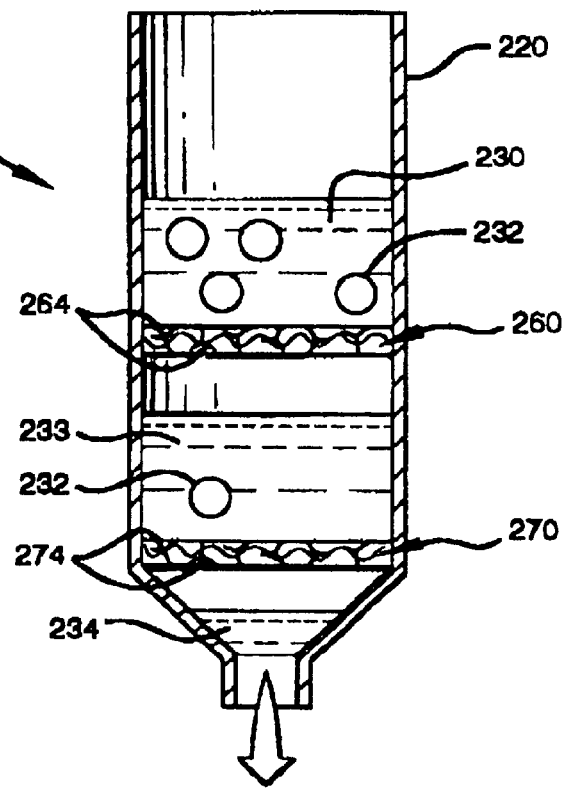
FIG. 3 is a schematic of another alternative embodiment.

In FIG. 3 a blood separation apparatus 210 has a vessel 220 that receives a blood sample 230, a pre-filter 260 coated with anti-red blood cell antibodies 264, and a secondary filter 270 coated with anti-red blood cell antibodies 274. A portion of the sample 230 has filtered through the pre-filter 260 to provide a partially cell-depleted fluid 233, and a portion of the cell-depleted fluid 233 has filtered through the secondary filter 270 to provide a substantially cell-depleted fluid 234.

Here, the vessel 220 is contemplated to be a vessel falling within bounds of vessels previously described with respect to vessel 20, and similar correspondences exist with respect to blood 230 and 30, red blood cells 232 and 32, primary antibodies 264 and 42, secondary antibodies 274 and 44, and plasma 234 and 34.

The preferred pre-filter material is nylon wool 260, comprising an uncompressed layer of nylon fibers. The secondary filter 270 is preferably a glass fiber disk onto which mouse anti-red blood cell antibodies 274 are bound. In alternative embodiments, either or both of the filters 260 and 270 can be substituted with any other suitable filter material including a fibrous filter material, filter paper, porous membranes etc. Examples hereof include coated or uncoated glass fibers, mineral wool, chromatographic paper etc. Furthermore, the filter material may or may not be coated e.g. to reduce hemolysis or to specifically retain selected fractions or molecules. Appropriate coatings include polyvinylalcohol, polyvinylacetate, polycationic polymers, lectins or antibodies other than that previously described.

EXPERIMENTS

Tests to separate red blood cells from plasma were performed, and the results are described below. These tests are only intended to be illustrative of some of the principles set forth above, and are not intended to be read as limitations on the scope of the claimed subject matter.

Experiment Set 1

In a first series of experiments, precipitation of red blood cells was performed using mouse anti-red blood cell antibodies, paramagnetic beads coated with goat anti-mouse antibodies and 0.5 ml of anti-coagulated whole blood. Heparinized, EDTA or citrated whole blood was mixed with 10 µl undiluted mouse anti-red blood cell antibody solution (Red Out™; Robbins Scientific Corp.) for 2 minutes; next 10 µl of a solution (isotonic PBS, pH 7.4) containing paramagnetic beads (Cortex Biochem Inc., MagaCell™ or MagaBeads™; 30 mg/mL; or Pierce MagnaBind™) coated with goat anti-mouse antibodies was added and mixed gently for 2 minutes. The bottom of the tube was placed on a magnet (permanent iron magnet; approximately 0.2 Tesla). Precipitation of the cellular network started instantly, and was substantially finished after about 2 minutes. Plasma was collected by aspiration from the top of the vessel.

Significantly, methods and apparatus described herein have been found to separate at least 70% (by volume) of the theoretically available cell-depleted portion from the network within a relatively short period of time. In many cases the time period for such 90% separation is less than 30 minutes, in other cases less than ten minutes, and in still other cases less than 2 minutes. Separations have also been performed using the methods described herein that achieve at least 80%, at least 90%, at least 95% and at least 98% of the theoretically available cell-depleted portion from the network within less than 30 minutes.

It should especially be appreciated that such separation characteristics and separation efficiencies may also be obtained using various cells other than red blood cells, and especially contemplated alternative cells include various stem cells, lymphocytes, and leukocytes.

Experiment Set 2

In a second series of experiments, precipitation of red blood cells on a microscope slide was performed using whole blood, mouse anti-red blood cell antibodies and paramagnetic beads coated with goat anti-mouse antibodies. To 0.2 ml fresh whole blood, 5 µl of an anti-red blood cell antibody containing solution (Red Out™) was added, mixed and incubated for 2 min at room temperature. Then, 5 µL of a solution containing paramagnetic beads coated with goat anti-mouse antibodies (MagaCell™ or MagaBeads™ or MagaBind™) was added, mixed, and after another 2 minutes, two disk magnets were positioned at opposite ends of the slide. After about 1.5 minutes, a clear plasma containing zone was formed between the two magnets and this was retrieved with a pipette without disturbing the laterally-fixed cell-containing network.

Experiment Set 3

Flat envelopes sealed on three of four sides were prepared from transparency acetate sheets (for example, the 3M Inc. product, 3MCG3460), or plastic sheet protectors (e.g., Avery-Dennison PV119E), or from small "ZipLock" or ITW Inc. MiniGrip™ bags (2.5×3 cm; 2.0 mil). One-half to 1 mL of anti-coagulated whole blood was injected into the bag; 10 uL of Red Out™ (see above) was added and mixed with blood by gently rocking the container. After 2 minutes, the anti-mouse coated magnetic beads (MagaCell™) were added, mixed and the open side of the bag sealed. Two minutes later the bag was placed horizontally on a rectangular permanent iron magnet (approximately 0.2 Tesla). The magnetic particles and attached cellular networked moved adjacent to the magnet, leaving a clear layer of plasma as supernatant. The bag was then rotated into an upright position while still on the magnet, opened, and plasma aspirated using a pipette. It was also discovered that envelopes or bags (containing blood previously treated with anti-RBC antibodies and anti-mouse coated paramagnetic beads) could be passed between two permanent magnets separated a narrow distance. As the sack was drawn upward between magnets, the cellular network was pulled to the bottom of the container, producing an overlying layer of plasma.

Thus, in this example a vessel retains a sample within a plurality of flexible confining walls, and a cell-containing network formed within the sample is separated within the plurality of confining walls. Alternatively, instead of passing the envelopes or bags between two magnets, compression of the bag utilizing actuators or other mechanical devices could be employed to move the cellular network relative to the vessel. In this case, a second force (i.e., an automatic mechanical force) is employed to separate the network from the substantially cell-depleted portion, wherein the second force is transmitted through at least one of the confining walls.

Experiment Set 4

In one experiment, a small amount of steel wool (washed and treated with 5 mg/mL BSA in PBS for 12 hours) was added to the sample container prior to addition of blood and precipitating reagents. After addition of RedOut™ and MagaCell™ reagents (each for 2 minutes), the tube was placed on the magnet. The paramagnetic beads contained within the cellular network were immobilized to the steel wool. A pipette tip was used for aspiration of plasma that was essentially free of blood cells. When coated with protein or some other polymer, the steel wool caused very little hemolysis in the cellular pellet in a 2-hr period. It is further contemplated that iron wire, wool, or beads could be added as above if it were coated with other non-hemolyzing polymers such as dextran, polyvinylpyrilidone on polyethylene glycol etc.

In another experiment, 15 iron brads were taped around the external bottom ⅓ of a 12 mm glass tube in which whole blood was incubated as described above with mouse anti-red blood cell antibodies and paramagnetic beads coated with goat anti-mouse antibodies. Placing the tube on a rectangular magnet produced an almost immediate deposition on the bottom and sides of the tube. The external brads place the magnetic source closer to the sample tube, thus applying a relatively uniform source of secondary lateral attraction to the entire sample column and as the cellular network moves to the sides of the tube, it aggregates further.

Experiment Set 5

Test results produced in accordance with methods and apparatus described herein are depicted in Table 1. In this regard it should be noted that centrifugation is at least 99% effective in removing cellular matter from whole blood, (99% separation efficiency) and that methods and apparatus described herein (listed as "Device" in the table) are almost as effective. In particular, methods and apparatus described herein can be described as having separation efficiency of least 90%, at least 95%, and at least 98%.

Thus, specific embodiments and applications of magnetic separation have been disclosed. It should be apparent to those skilled in the art, however, that many more modifications besides those already described are possible without departing from the inventive concepts herein. The inventive subject matter, therefore, is not to be restricted except in the spirit of the appended claims.

What is claimed is:

1. A method of separating a target cell-containing sample into a substantially target cell-depleted portion, and a target cell-containing portion comprising at least one of a stem cell, a lymphocyte, and a leukocyte, comprising:

receiving the sample in a vessel, wherein the vessel retains the sample within a plurality of confining walls, and wherein at least one of the confining walls is flexible;

providing an additive and magnetic particles, wherein the additive binds to the at least one of the stem cell, lymphocyte, and leukocyte, and the magnetic particles, and wherein the magnetic particles bind to the at least one of the stem cell, lymphocyte, and leukocyte, and the additive;

combining the sample, the additive, and the magnetic particles to produce a target cell-containing network; and separating the network within the plurality of confining walls from the target cell-depleted portion by applying a first and a second force, wherein the first force is a magnetic force and the second force is an automatic mechanical force that is transmitted through at least one of the confining walls.

2. The method of claim 1 wherein the target cell-containing portion comprises a stem cell.

3. The method of claim 2 wherein the stem cell is selected from the group consisting of an embryonic stem cell, an adult stem cell, and a partially differentiated stem cell.

4. The method of claim 3 wherein the stem cell has a surface marker selected from the group consisting of SSEA-3, SSEA-4, TRA-1-60, and TRA-1-81.

5. The method of claim 1 wherein the sample received in the vessel has a volume of between about 10 ml and 100 ml.

6. The method of claim 1 wherein the sample received in the vessel has a volume of between about 100 ml and 500 ml.

7. The method of claim 1 wherein the particles are coated with a coating.

8. The method of claim 7 wherein the coating comprises an anti-ligand.

9. The method of claim 7 wherein the coating comprises an antibody.

10. The method of claim 1 wherein the magnetic particles comprise a primary antibody and the additive comprises a secondary antibody, and wherein the primary antibody binds to a surface component of the at least one of the stem cell, lymphocyte, and leukocyte, and wherein the secondary antibody binds to the primary antibody.

11. The method of claim 1 wherein separating the network produces a separation efficiency of at least 90%.

12. The method of claim 1 wherein at least 90% by volume of the cell depleted portion is separated from the network within ten minutes, with a separation efficiency of at least 95%.

TABLE 1

| | Plasma Volume mL | | PSA Ng/mL | | Testosterone ng/mL | | Creatinine mg/dL | | Hemoglobin g/dL | | Plasma Hematocrit % | | Red Blood Cells millions/uL | | White Blood Cells thousands/uL | |
|---|---|---|---|---|---|---|---|---|---|---|---|---|---|---|---|---|
| Subject | Centrifugation | Device | Centrifugation | Device | Centrifugation | Device | Centrifugation | Device | Centrifugation | Device | Centrifugation | Device | Centrifugation | Device | Centrifugation | Device |
| 1 | 0.45 | 0.36 | 28.5 | 27.2 | 4.78 | 5.45 | 0.75 | 0.64 | 0.27 | 0.16 | | | | | | |
| 2 | 0.55 | 0.48 | 25.1 | 23.2 | 14.45 | 11.2 | 0.70 | 0.62 | 0.27 | 0.19 | | | | | | |
| 3 | 0.53 | 0.48 | 27.2 | 26.4 | 16.19 | 15.18 | 1.04 | 1.06 | 0.38 | 0.24 | | | | | | |
| 4 | 0.48 | 0.40 | 26.9 | 24.8 | 11.18 | 10.96 | 0.97 | 0.91 | 0.25 | 0.15 | | | | | | |
| 5 | 0.57 | 0.51 | 25.9 | 24.2 | | | 0.84 | 0.91 | 0.48 | 0.13 | | | | | | |
| 6 | | | 21.3 | 20.2 | 10.97 | 10.15 | 1.11 | 1.10 | 0.12 | 0.05 | <0.1 | <0.1 | 0 | 0 | 0.2 | 0.1 |
| 7 | | | 25.2 | 23.6 | 6.08 | 7.58 | 0.69 | 0.72 | 0.16 | 0.08 | <0.1 | <0.1 | 0 | 0 | 0.2 | 0.2 |
| 8 | | | 25.5 | 20.4 | 18.06 | 22.79 | 0.99 | 0.91 | 0.22 | 0.09 | <0.1 | <0.1 | 0 | 0.02 | 0.2 | 0.2 |
| 9 | | | 16.4 | 16.6 | 0.46 | 0.27 | 1.35 | 1.49 | 0.33 | 0.17 | <0.1 | <0.1 | 0 | 0 | 0.2 | 0.2 |